United States Patent [19]
Bourguignon

[11] Patent Number: 5,804,550
[45] Date of Patent: Sep. 8, 1998

[54] PEPTIDE ANTAGONISTS AT GLUTAMATE AND NMDA RECEPTORS

[75] Inventor: J. P. Bourguignon, Liége, Belgium

[73] Assignee: Pharmacia & Upjohn Aktiebolag, Stockholm, Sweden

[21] Appl. No.: 549,798

[22] Filed: Nov. 9, 1995

[30] Foreign Application Priority Data

May 14, 1993 [SE] Sweden ................................. 9301667

[51] Int. Cl.$^6$ .......................... A61K 38/00; A61K 38/28; A61K 38/27; A61K 38/04
[52] U.S. Cl. .................................... 514/3; 514/4; 514/12; 514/13
[58] Field of Search ................................. 514/3, 4, 12, 13

[56] References Cited

U.S. PATENT DOCUMENTS 5,017,557  5/1991  Fabbri et al. ............................. 514/12

FOREIGN PATENT DOCUMENTS 9118621     12/1991  WIPO .
WO 93/02695  7/1993  WIPO .

OTHER PUBLICATIONS

Sara et al., Identification of Gly–Pro–Glu (GPE), The Aminoterminal Tripeptide of Insulin–Like Growth Factor 1 which is Truncated in Brain, as a Novel Neuroactive Peptide, Biochemical and Biophysical Research Communications, vol. 165, No. 2, 1989, pp. 766–771.

Szabo et al., The Bovine Insulin–Like Growth Factor (IGF) Binding Protein Purified from Conditioned Medium Requires the N–Terminal Tripeptide in IGF–1 for Binding Biochemical and Biophysical Research Communications, vol. 151, No. 1, 1988, pp. 207–214.

Hiney et al., Insulin–Like Growth Factor I: A Possible Metabolic Signal Involved in the Regulation of Female Puberty[1], Rapid Communication, Neuroendocrinology, 1991, vol. 54, pp. 420–423.

Bourguignon et al., Gonadal–Independent Development Changes in Activation of N–Methyl–D–Aspartate Receptors Involved in Gonadotropin–Releasing Hormone Secretion, Neuroendocrinology 1991, vol. 55, pp. 634–641.

Carone et al., Differences between in vitro and in vivo degradation of LHRH by rat brain and other organs, American Journal of Phys., vol. 253, 1987, pp. E317–E321.

Sasaki et al., Multiple Forms of Immunoreactive Growth Hormone–Releasing Hormone in Human Plasma, Hypothalamus, and Tumor Tissues, Journal of Clinical Endocrinology and Metabolism, vol. 68, No. 1, pp. 180–185.

Bourguignon et al., Gonadotropin releasing hormone inhibitory autofeedback by subproducts antagonist at N–methyl–D–aspartate receptors: a mode of autocrine regulation of peptide secretion, Chemical Abstracts, vol. 120:208955u, 1994, p. 148.

Primary Examiner—Cecilia J. Tsang
Assistant Examiner—P. Lynn Touzeau
Attorney, Agent, or Firm—Pollock, Vande Sande & Priddy

[57] ABSTRACT

The invention relates to the use of a new type of peptide antagonists at glutamate receptors and a subtype of glutamate receptors (NMDA (N-methyl-D-aspartate)) for the manufacture of a medicament to influence the glutamate receptor and the NMDA-receptor controlled cells such as neurons or glial cells in the central nervous system.

11 Claims, 14 Drawing Sheets

Figure 5C:
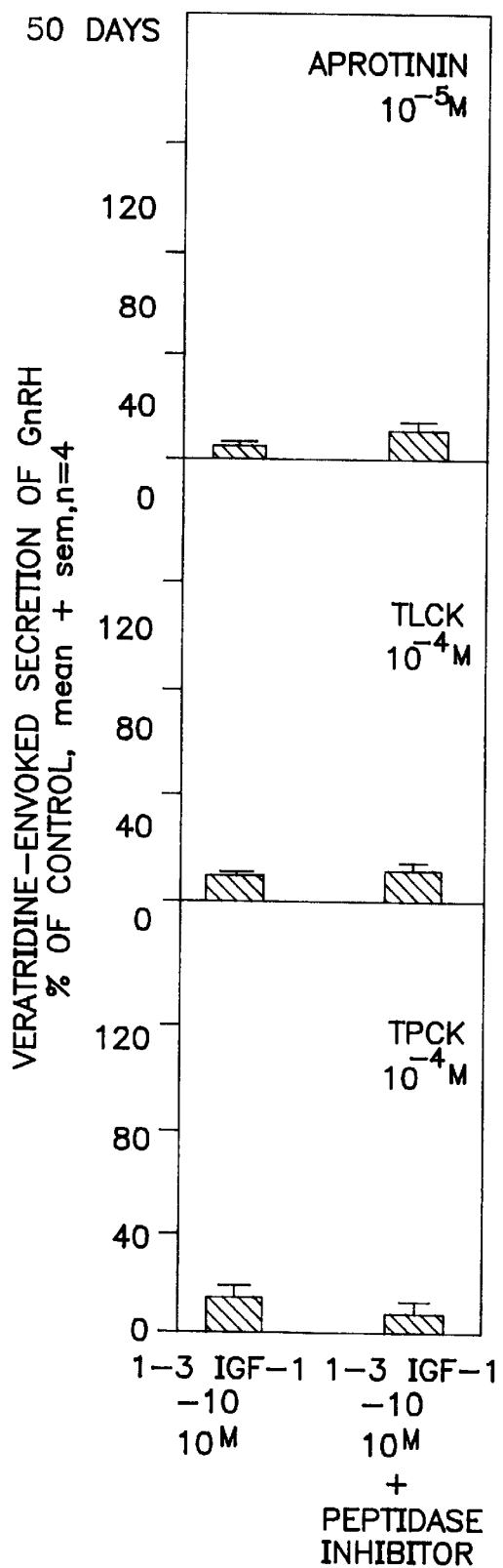

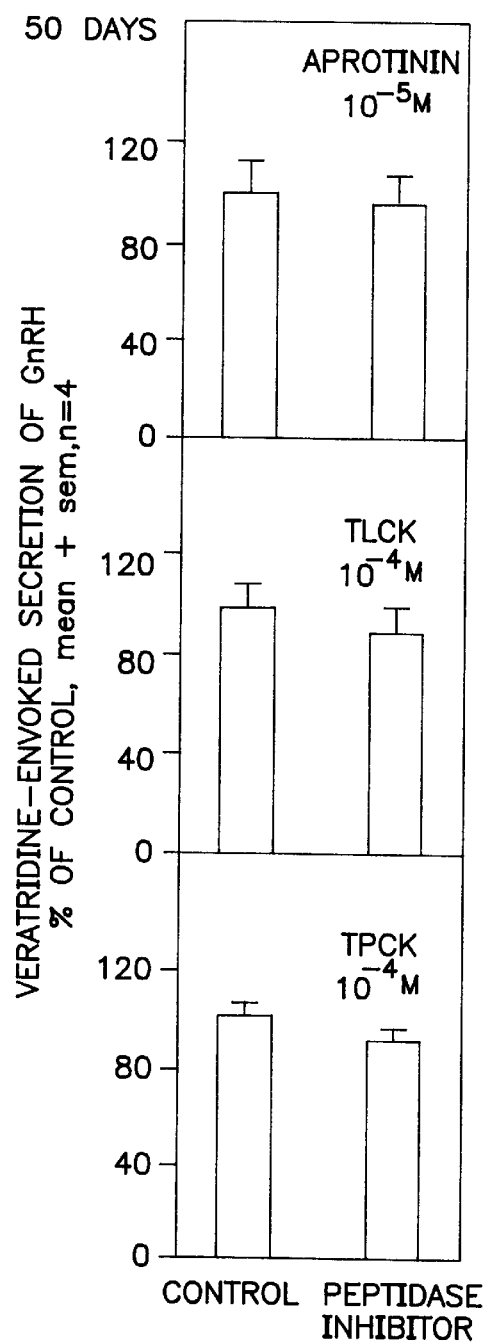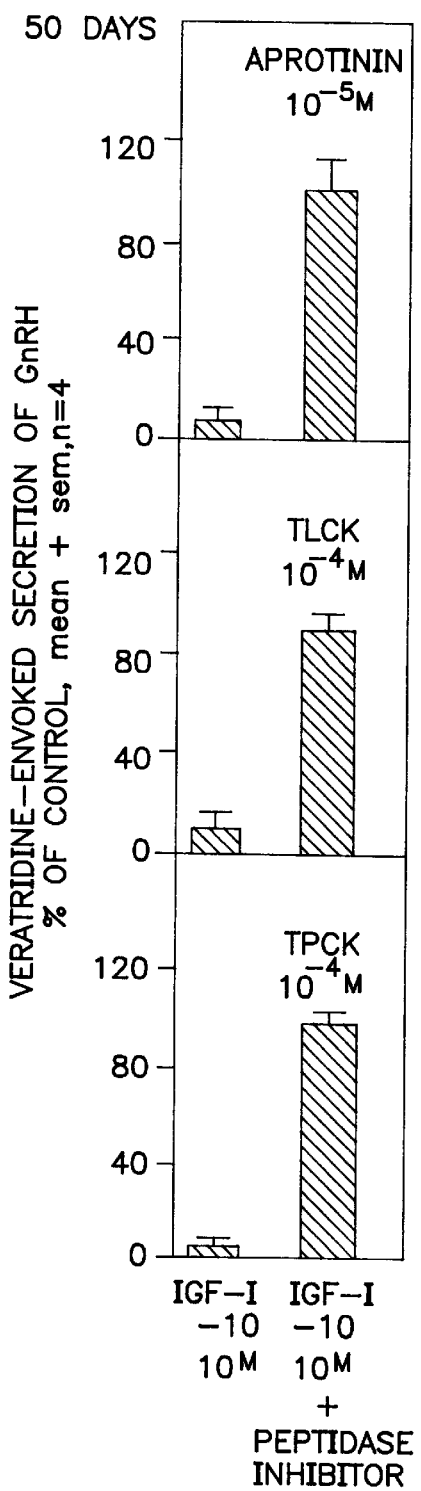
FIG. 5A
FIG. 5B

PEPTIDE ANTAGONISTS AT GLUTAMATE AND NMDA RECEPTORS

The invention relates to the use of a new type of peptide antagonists at glutamate receptors and a subtype of glutamate receptors (NMDA (N-methyl-D-aspartate)) for the manufacture of a medicament to influence the glutamate receptor- and the NMDA-receptor-controlled cells, such as neurons or glial cells in the central nervous system. The medicament comprises glutamic acid-terminating peptides, such as (1–5)GnRH, (1–3)IGF-I, (1–37)GRF and C-peptide of insulin. The medicament could be used for the treatment of hypoxic, ischemic and metabolic insults to the central nervous system, such as stroke, hypoglycaemia, traumatic, radiation-induced or inflammatory injuries as well as chronic degenerative states of the brain in adult or paediatric patients.

INTRODUCTION

It is known that the receptors to the neuroexcitatory amino acid, glutamate, particularly the N-methyl-D-aspartate (NMDA) subtype of receptor, play a critical role in development, function and death of neurons. (Mc Donald J W et al, Brain Research Reviews, 1990. 15:41–70 and Choi W, Neuron 1988, 1:623–34).

It is also known that the secretion of the neuropeptide GnRH (Gonadotropin-releasing hormone) is dependent on the activation of NMDA receptors. Therefore, the GnRH neurosecretory system can provide a sort of bioassay of NMDA receptor activation and inhibition. It can be referred to previous work on this matter. (1–3)

Insulin-like growth factor-I (IGF-I) has raised considerable interest as a possible regulator of neuronal and glial cell development and function (4). However, the mechanism of its paracrine action in the brain is not fully elucidated. In addition, endocrine effects on the brain possibly resulting from the age-related increase in peripheral serum concentrations of IGF-I (5) are still putative. In the fetal brain, Sara et al have shown the presence of a N-terminal-truncated and bioactive form of IGF-I(6). This led these authors to hypothesize that brain IGF-I could be degraded into (4–70)IGF-I retaining IGF-I bioactivity (7), and (1–3)IGF-I, the N-terminal tripeptide.

More recently, Sara et al have suggested that (1–3)IGF-I could modulate acetylcholine release from cortical slices through an unknown mechanism. In addition, these authors suggested that (1–3) IGF-I could act as an agonist at NMDA receptors involved in dopamine release from striatal slices. (8). They suggested that IGF-I could be the precursor of an endogenous NMDA receptor agonist. Since we showed earlier that NMDA receptors were involved in the mechanism of GnRH secretion (1, 2) with changes related to age and puberty (3, 9), we aimed to study the possible effects of IGF-I and its subproducts on GnRH secretion from rat hypothalamic explants at different ages. In addition, we compared the effects of the systemic administration of these peptides in-vivo to those obtained after their local use in-vitro.

INVENTION

The invention relates to the use of peptide antagonists at glutamate receptors and NMDA receptors (a subtype of glutamate receptor) for the manufacture of a medicament to influence glutamate receptor-controlled cells and NMDA-receptor-controlled cells, preferably neurons or glial cells in the central nervous system. The medicament prevents NMDA receptor mediated excitatory effects such as release of neurotransmitter or peptide and toxic effects responses resulting in cell injury or cell death following massive calcium influx.

Thus the invention relates to a method to influence therapeutically the secretion, function and death of glutamate (NMDA)-receptor-controlled cells.

The medicament comprises glutamic acid-terminating peptides, preferably chosen among (1–5)GnRH, (1–3)IGF-I, (1–37)GRF and C-peptide of insulin. Preferably the medicament comprises (1–3) IGF-I.

The medicament has been shown to influence GnRH secretion through NMDA receptor antagonism.

The medicament could be used for the treatment of disorders involving excessive activation of NMDA receptors such as acute or chronic disorders of the central nervous system, hypoxic, ischemic and metabolic brain disorders including stroke and hypoglycaemia, traumatic, radiation-induced of inflammatory injuries to the brain and chronic degenerative states. The connection between NMDA receptors and hypoxic ischemic and metabolic disorders is e.g. disclosed in Simon R P et al, Sience 1984, 226:850–52, Wielocht, Science 1985, 230:681–83, Mc Donald J W et al, Brain Research Reviews, 1990.15:41–70, Choi W, Neuron 1988, 1:623–34. The treatment of children during the perinatal period and infancy is of importance with respect to neuronal development. The medicament could be administered systemically or locally. The medicament should be given in a therapeutic dose. Preferred doses could be in the range of 1 μg–10 mg/kg and preperably 5–50 μg/kg when (1–3)IGF-I is given systemically. The dose could be 0.1 μg to 1 mg/kg when (1–3)IGF-I is given locally.

The invention also relates to a method for treatment as defined in the claims.

Data given below show e. g. that:
a) (1–3) IGF-I acts as an NMDA-receptor antagonist
b) This effect can be obtained with the precursor peptide IGF-I indicating endogenous processing into the bioactive subproduct.
c) This mechanism operates after in-vivo administration
d) The examples relating to (1–3) IGF-I, GnRH and (1–5)GnRH are prototypes of a more general process involving glu-terminal subproducts of peptides.

Figures 1A, 1B:
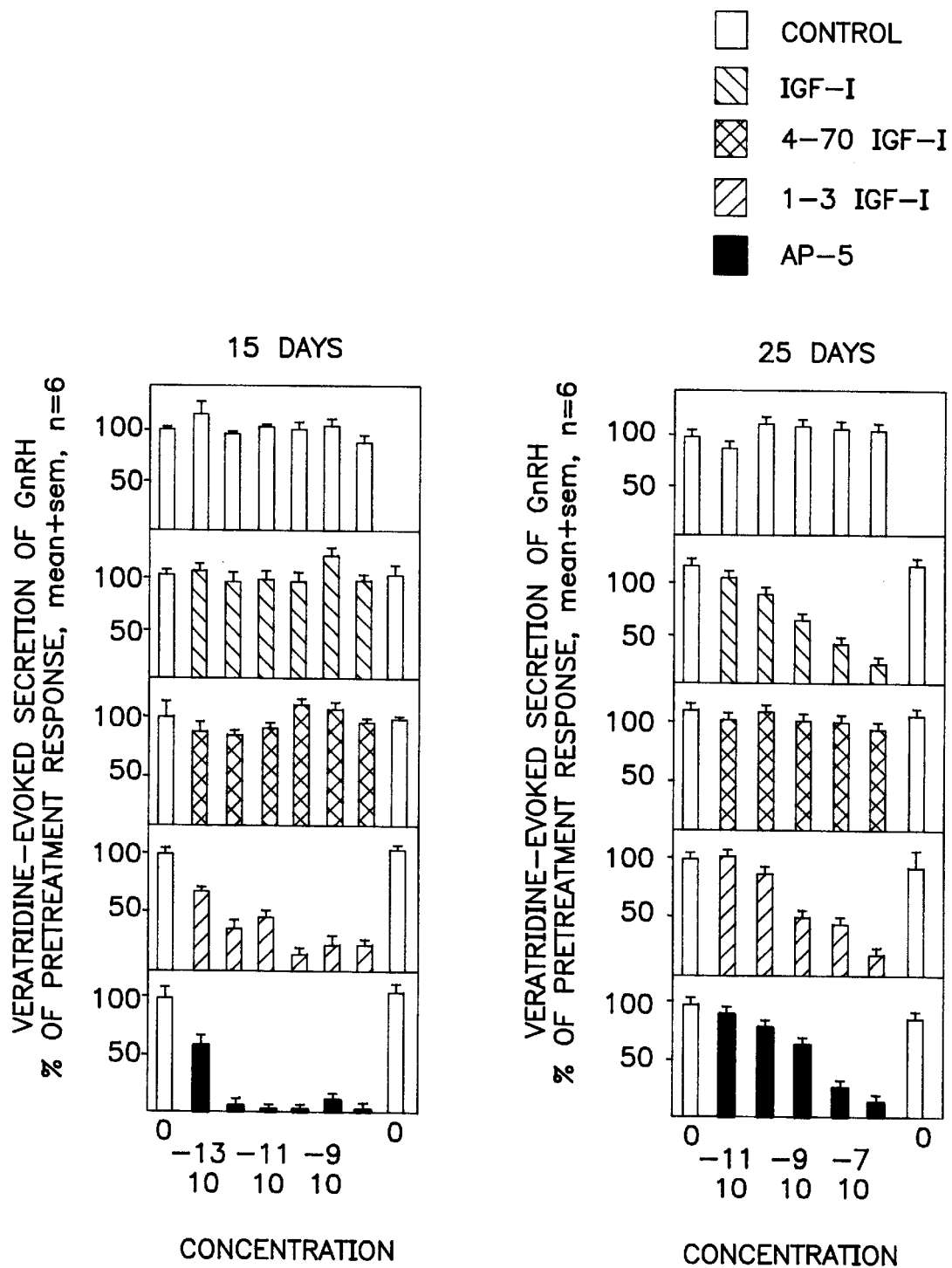
Figure 1C:
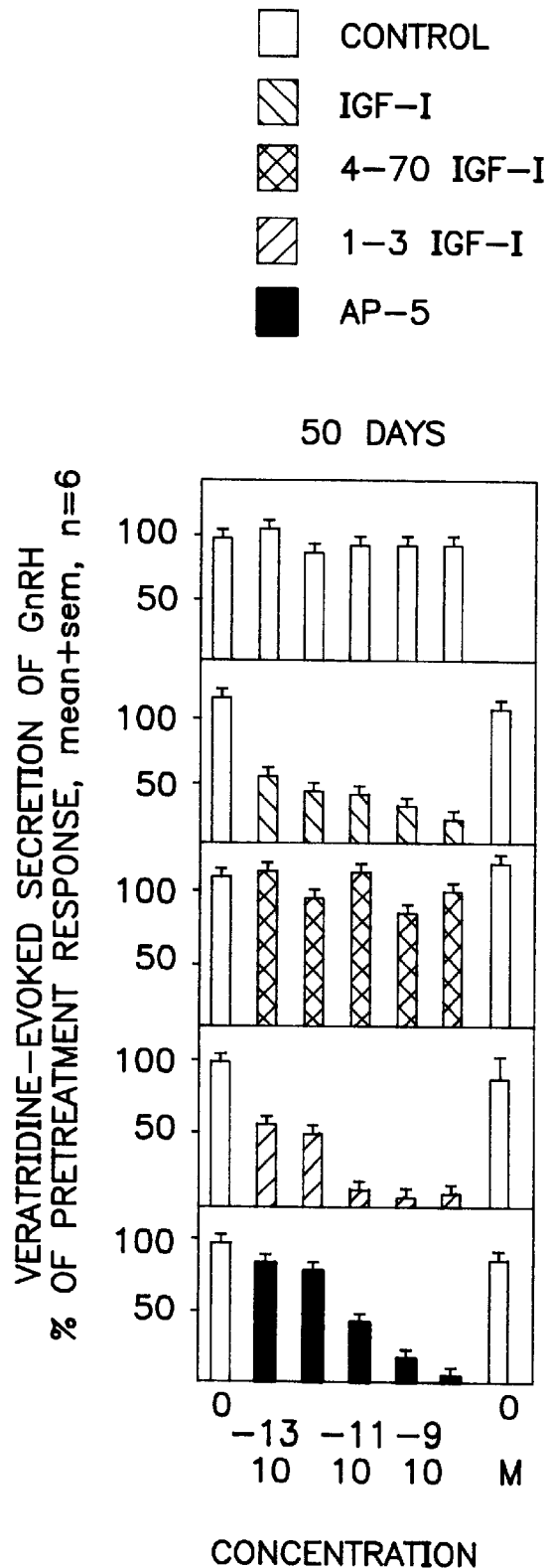

The following figures are included in the specification:

FIG. 1(a–c): In vitro effects of IGF-I-related peptides on GnRH secretion by hypothalamic explants at 15, 25 and 50 days.

Figure 2:
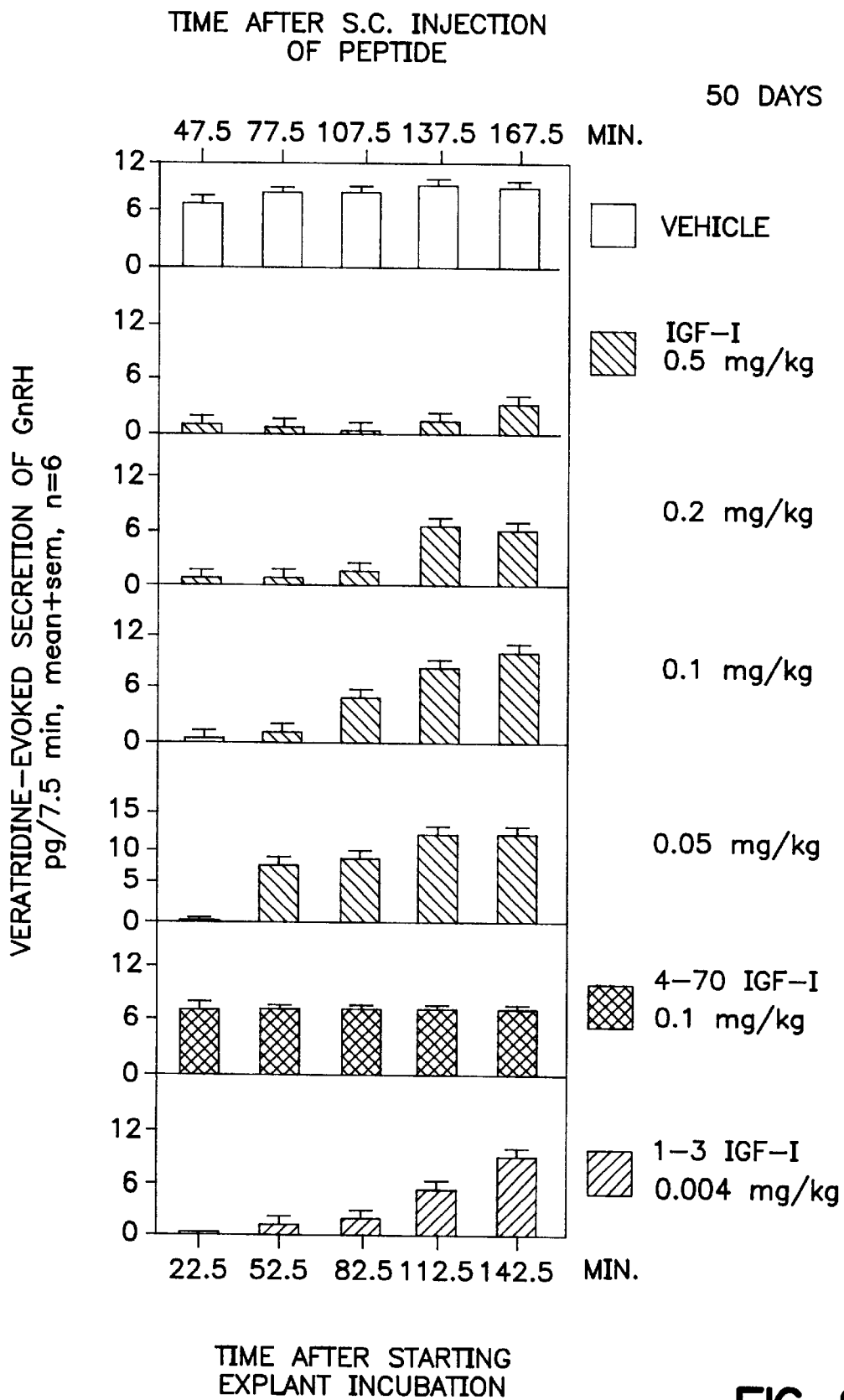

FIG. 2: Ex vivo effects of IGF-I-related peptides on GnRH secretion by hypothalamic explants at 50 days.

Figures 3A, 3B:
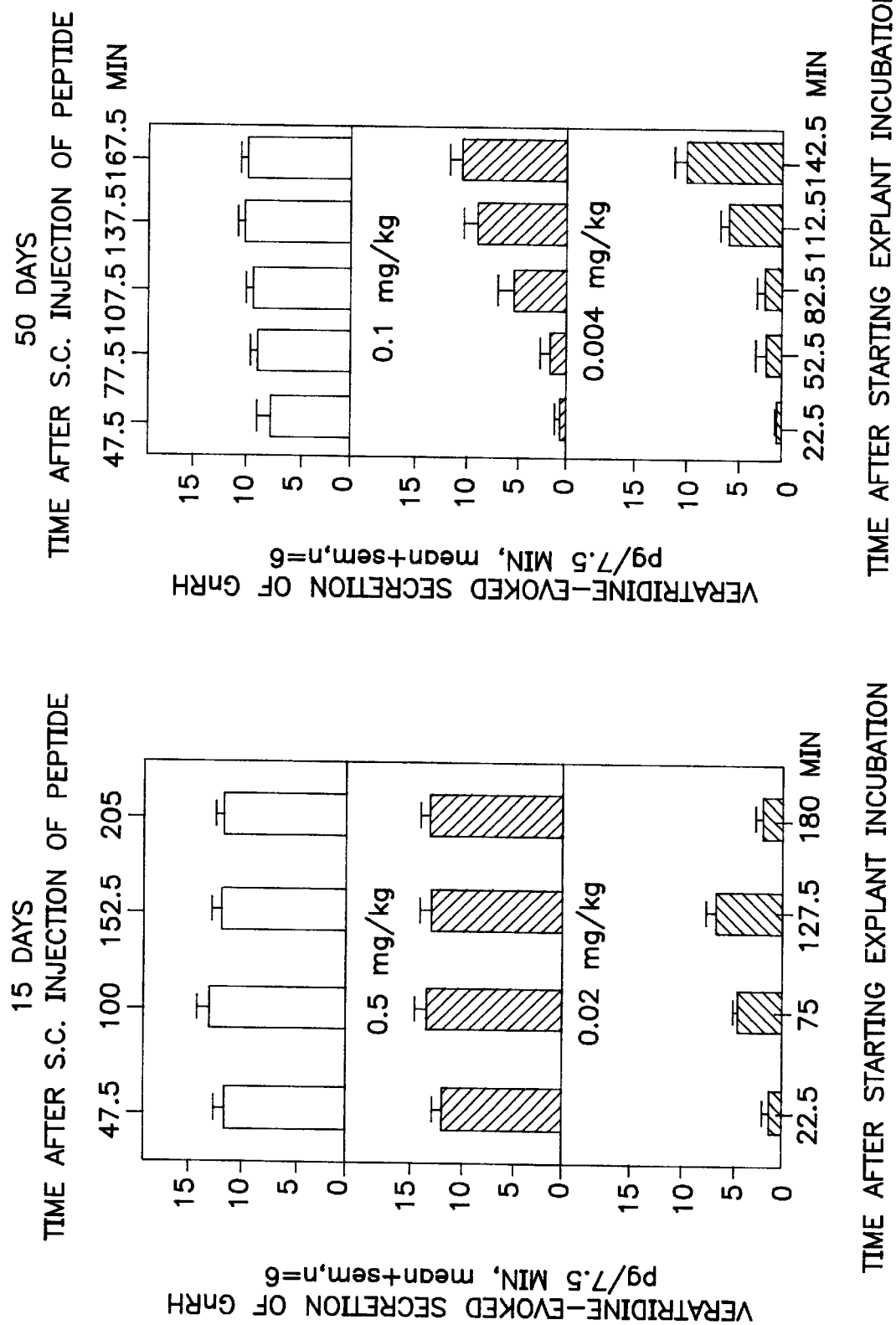

FIG. 3(a–b): Ex vivo effects of IGF-I-related peptides on GnRH secretion by hypothalamic explants at 15 and 50 days FIG. 4(a–b): In vitro effects of IGF-I on the secretion of GnRH by hypothalamic explants at 15 and 50 days FIG. 5(a–c). In vitro effects of IGF-I and (1–3)IGF-I on GnRH secretion by hypothalamic explants in the presence of peptidase inhibitors.

Figure 6A:
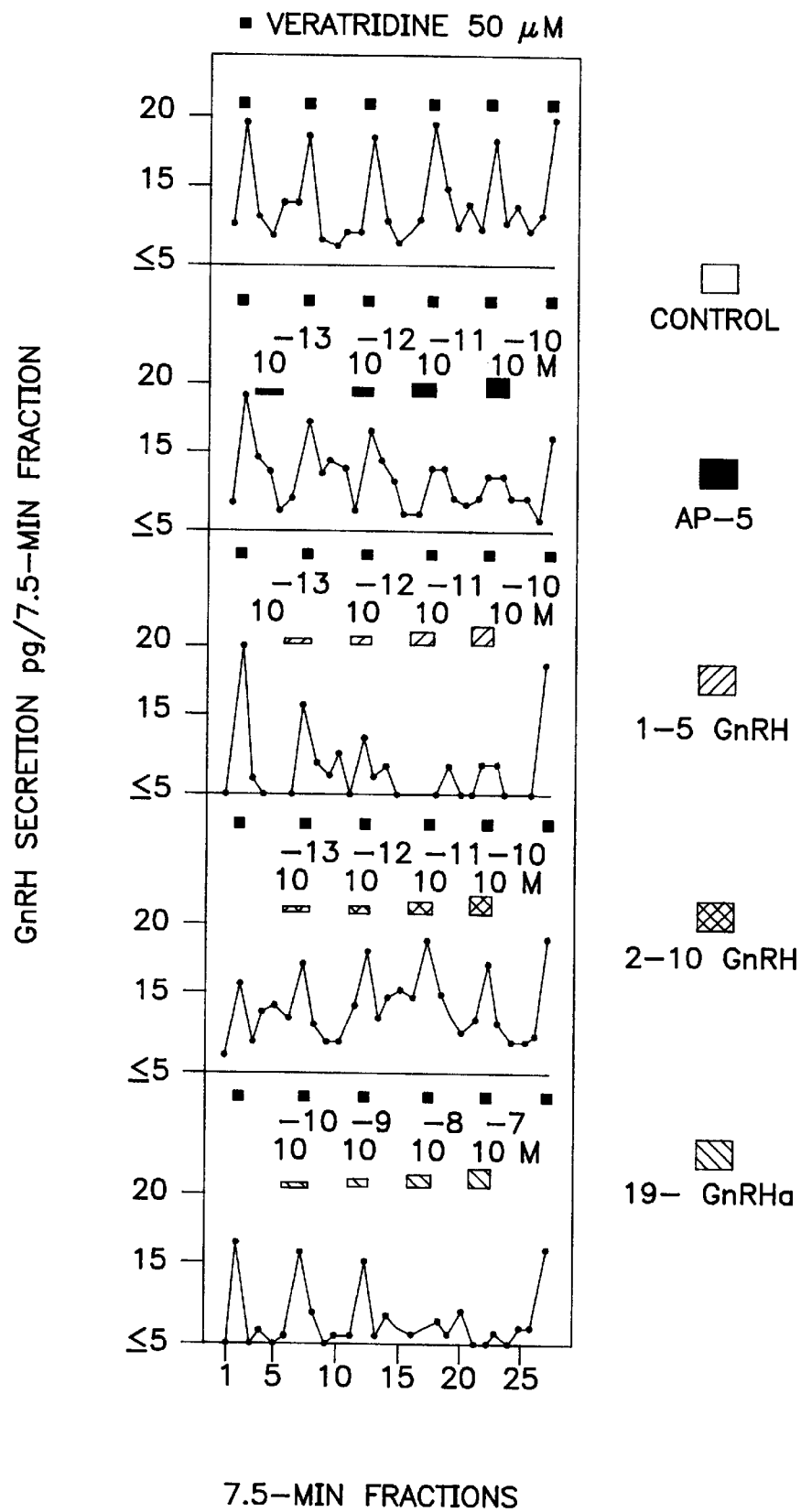
Figure 6B:
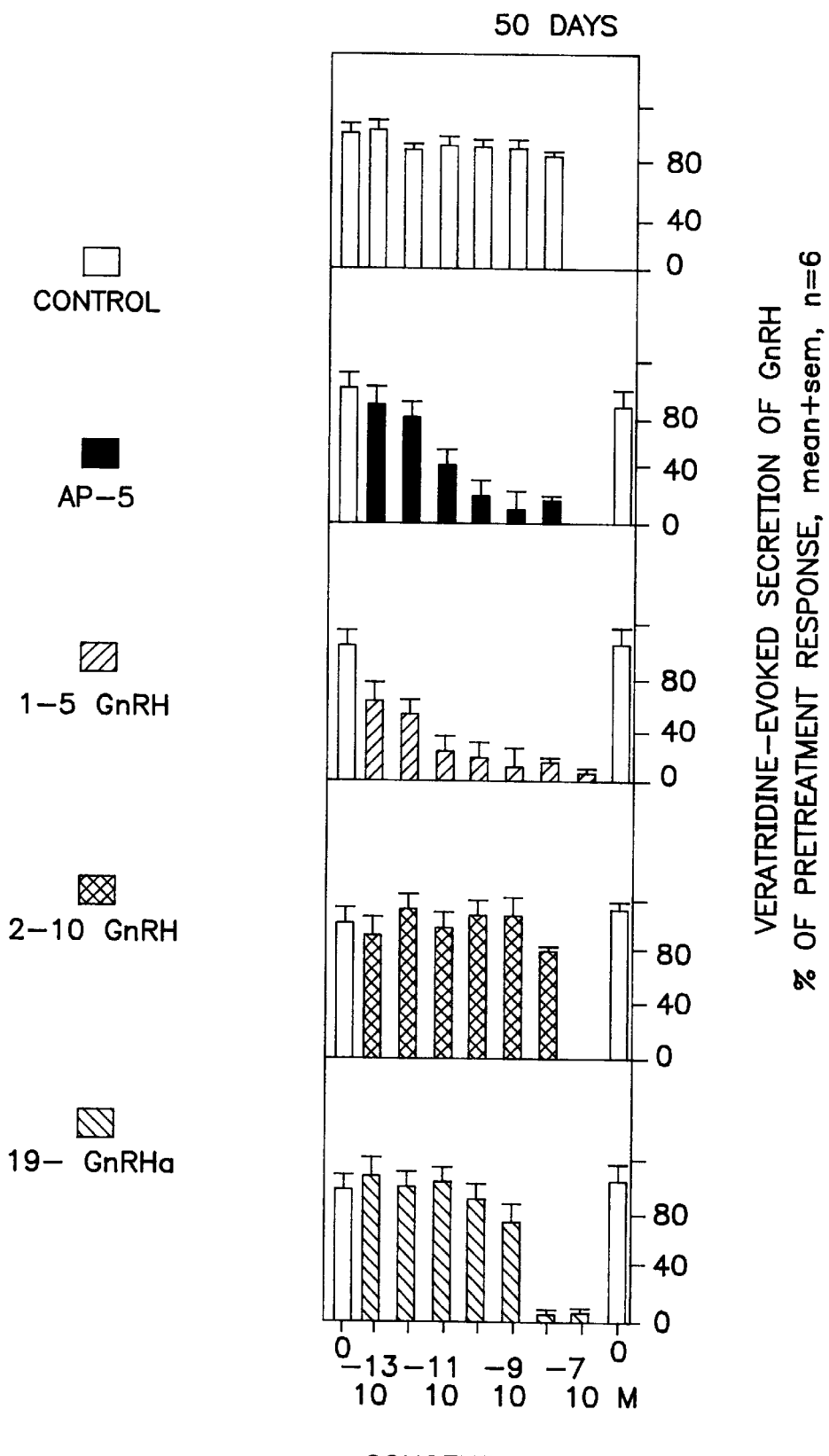

FIG. 6(a–b): In vitro effects of GnRH-related peptides on GnRH secretion by hypothalamic explants.

Figure 7A:
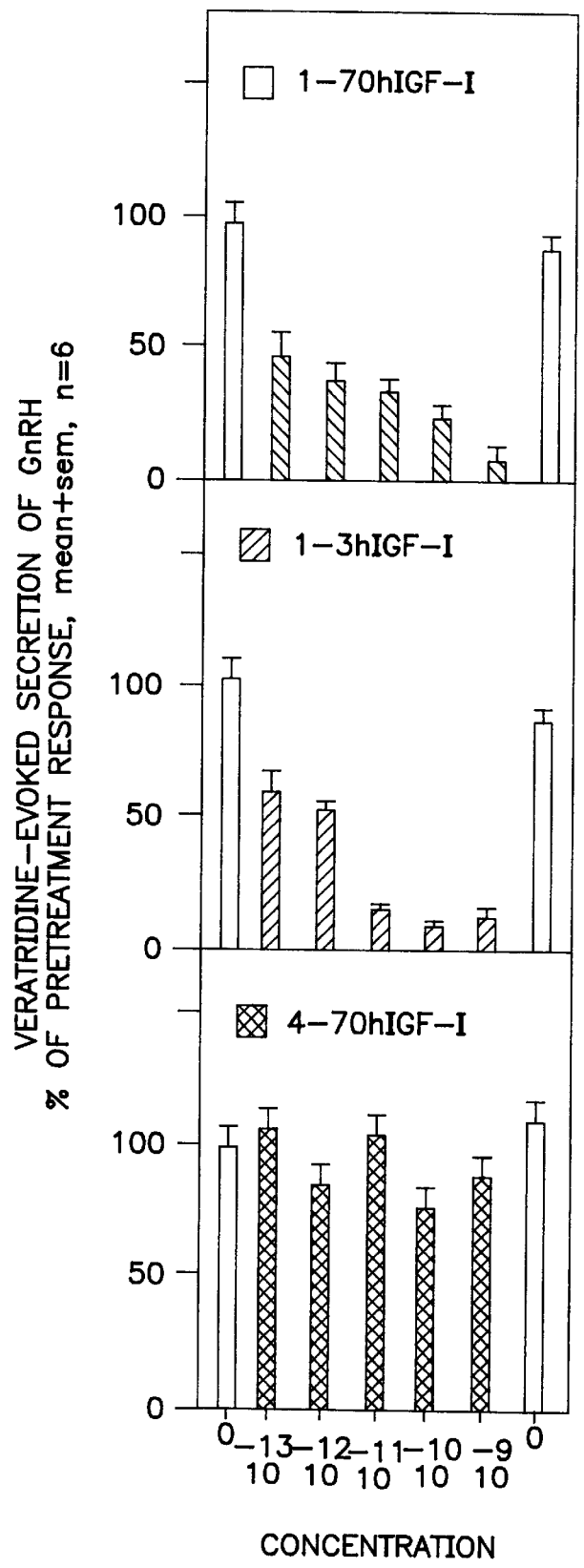
Figure 7B:
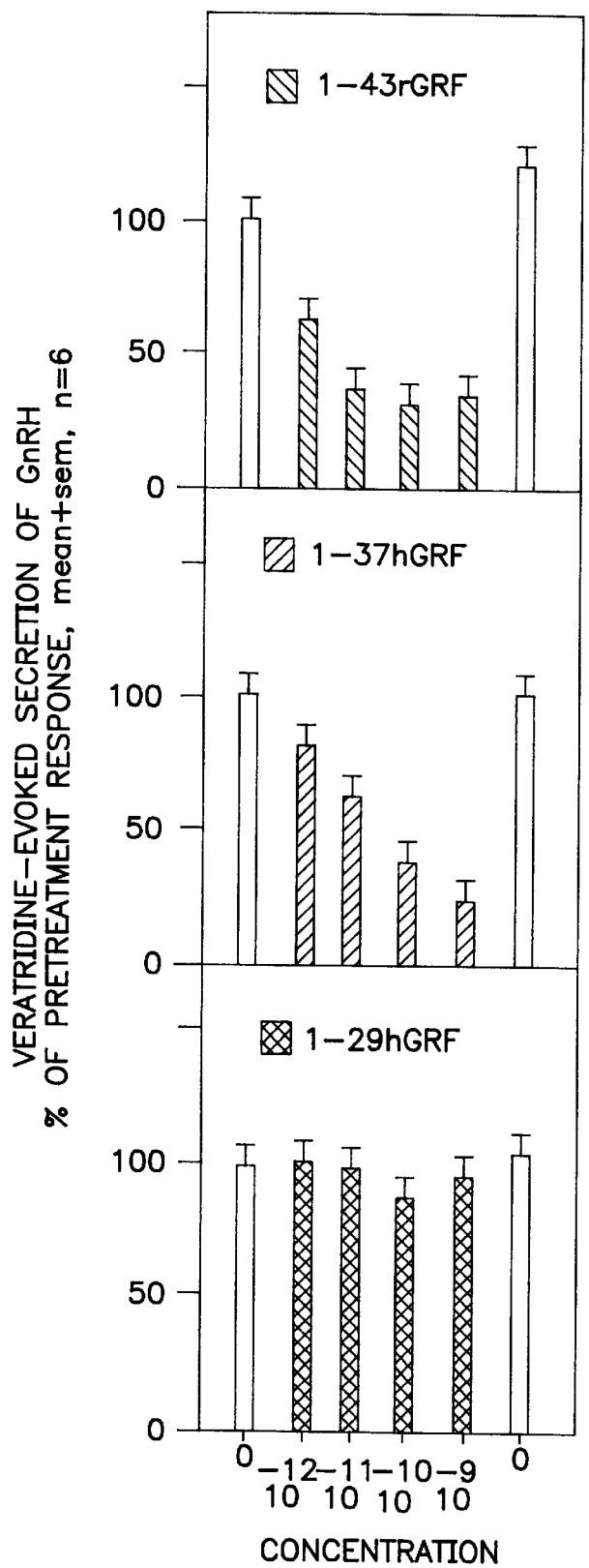
Figure 7C:
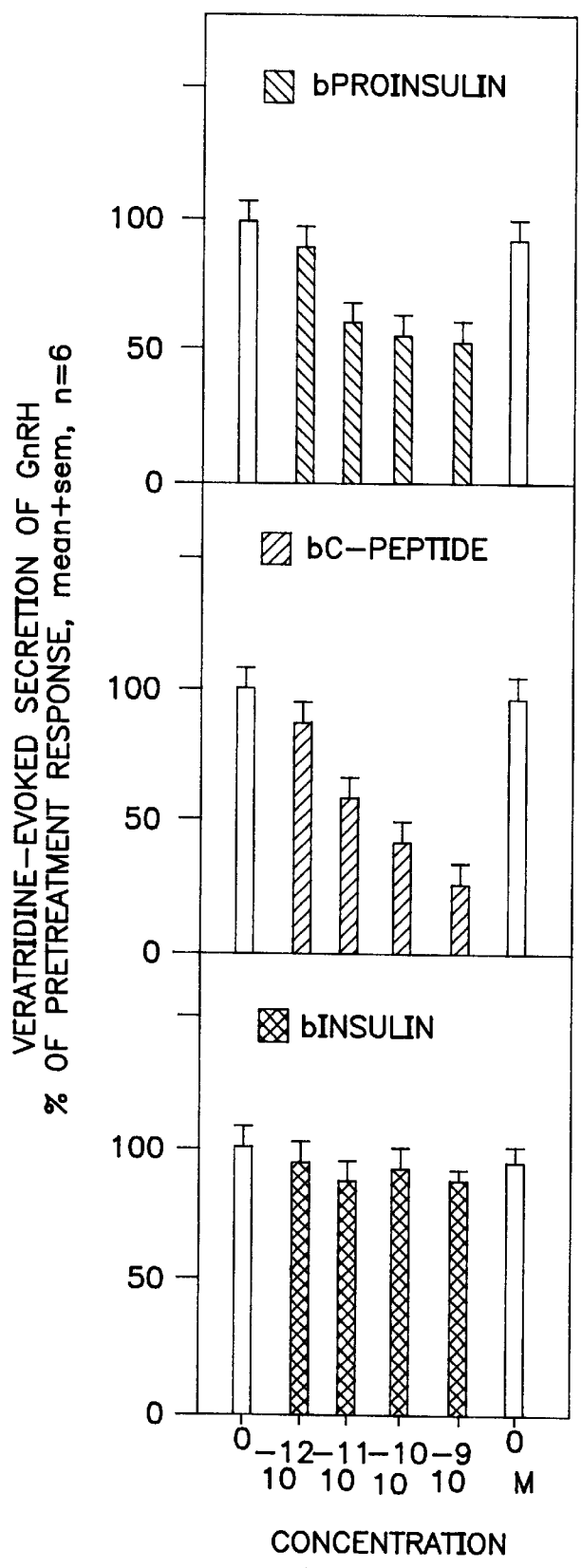

FIG. 7(a–c): In vitro effects of IGF-I, GRF-and Insulin-related peptides on the secretion of GnRH by hypothalamic explants.

Figure 8A:
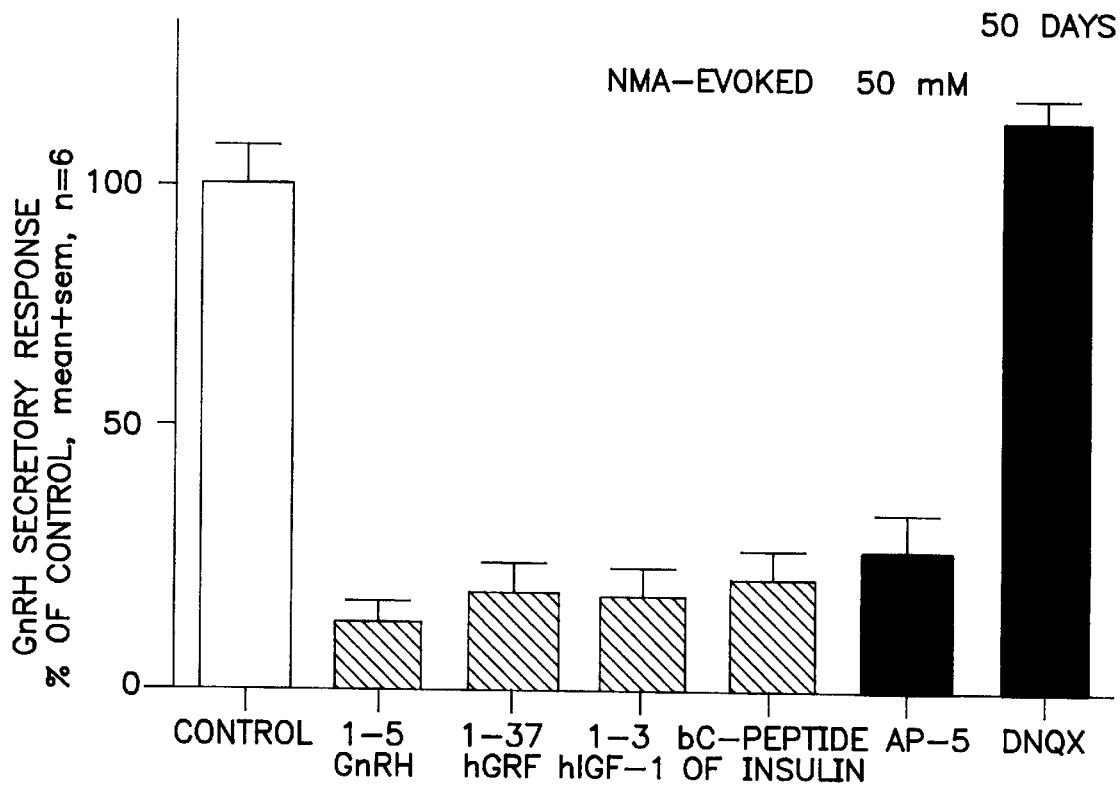
Figure 8B:
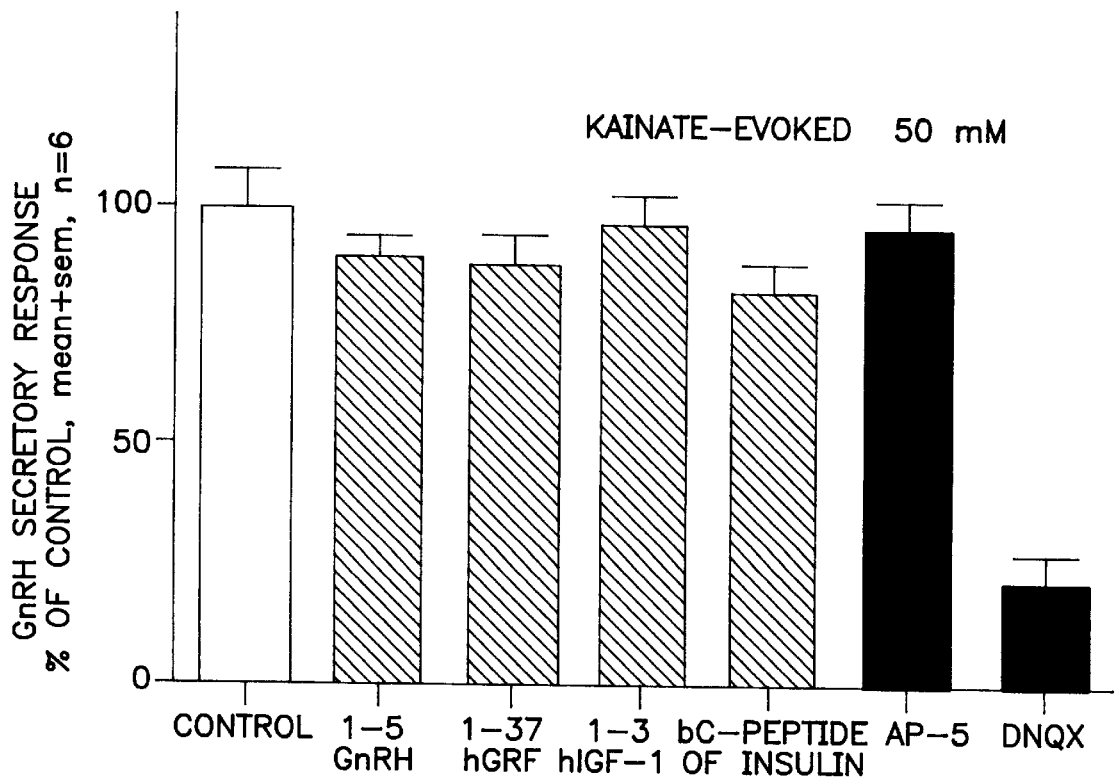

FIG. 8(a–b). In vitro effects of glutamic acid-terminating peptides on GnRH secretion induced by NMA and kainate from hypothalamic explants.

Figure 9:
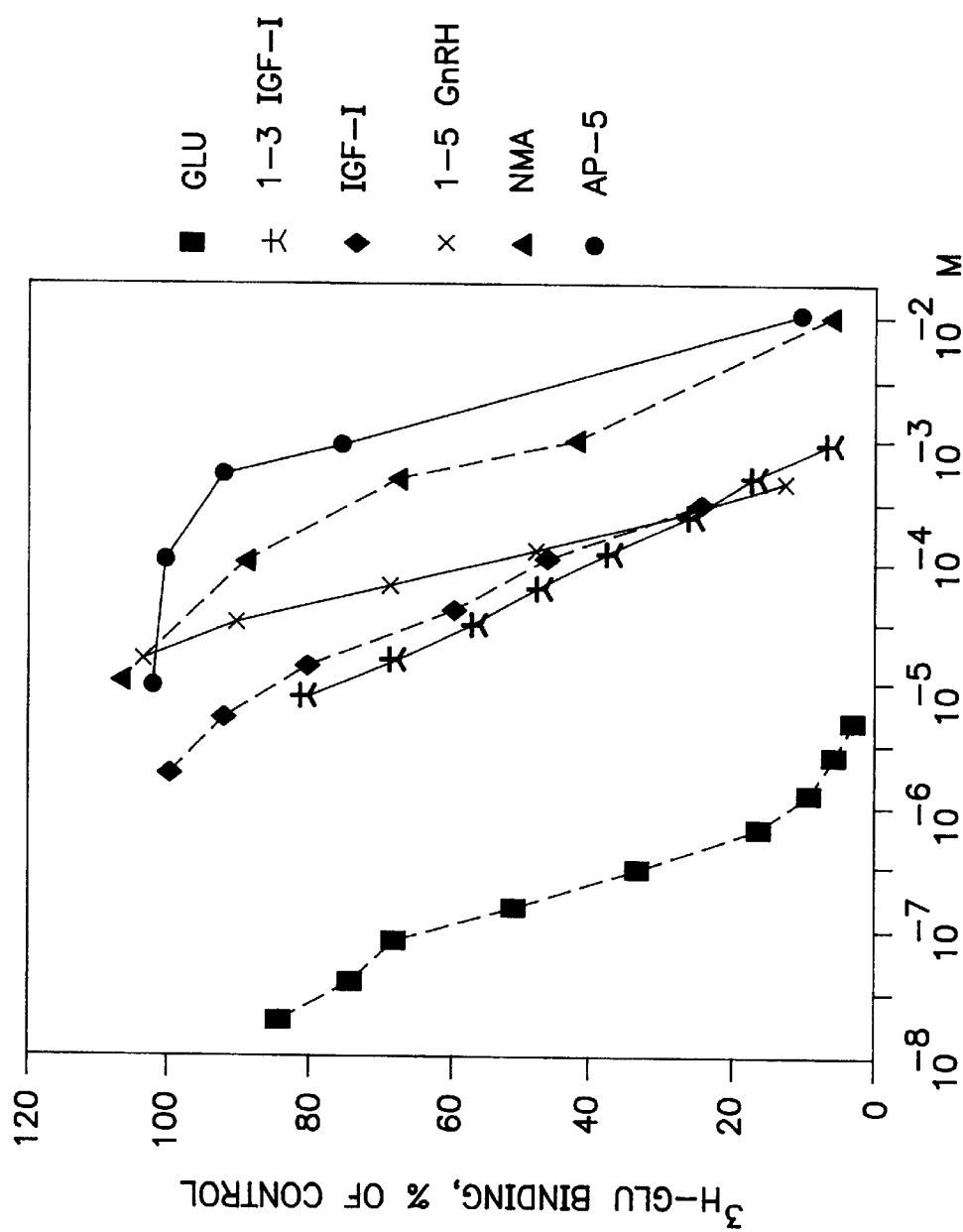

FIG. 9: Displacement of tritiated glutamate from hypothalamic membrane by different compounds.

We have tested the hypothesis that glutamic acid-terminating products belonging to peptide systems different from IGF-I could also act as antagonist at NMDA receptors. We have studied (1–5) GnRH, a peptide with a N-terminal glutamic acid which results from the degradation of GnRH in the hypothalamus (10). Such a peptide could be involved in the inhibitory autofeedback of GnRH, a regulatory process that we described earlier (11). Growth Hormone-Releasing Factor (GRF) is another hypothalamic peptide possibly under the control of NMDA receptors as suggested by the stimulatory effect of NMDA on GH secretion (12). We have here studied (1–37)GRF, a minor physiological form with a C-terminal glutamic acid which was identified in human plasma or some tissues (13). In order to study a peptide system external to the brain, we have evaluated the effect of C-peptide of insulin, a subproduct of insulin with a C-terminal glutamic acid. While the NMDA subtype of glutamate receptors have not been localised in the pancreas so far, it is noteworthy that glutamic acid decarboxylase has been characterised recently as a major antigen from pancreatic islets (14). Glutamate receptors of the AMPA subtype have been localized in pancreas as well. (Bertrand et al. Br.J. Pharmacol., 1992, 101:354–9)

The inventive idea behind the present patent application is thus that there is an endogenous system of peptide antagonists at glutamate receptors. NMDA receptor representing a subclass of glutamate receptors can provide a basis for considering its therapeutic use. Three factors should thereby be taken into consideration:

1. Different peptides are physiologically present in the body as glutainc acid-terminating sequences of amino acids which can be the subproducts of other peptides. Considering 4 peptide systems, (GnRH, IGF-I, GRF, proinsulin), there are physiological subproducts that we show to be active as antagonists at NMDA receptors: (1–5)GnRH, (1–3)IGF-I, (1–37)GRF and C-peptide of insulin.

2. The second factor to take into account is the production of such glutamate-terminating peptides. Using IGF-I and (1–3)IGF-I, evidence is provided that the endogenous antagonists may not be produced at any age. This is critical in choosing between the precursor peptide or the antagonist itself for a therapeutic use, particularly in younger subjects such as preterm or fullterm neonates. Based on our experimental data, it is possible that newborns have less or no ability to make such peptide antagonists, at least for IGF-I.

3. The third factor is the possible endocrine delivery of such antagonists to the brain. This is critical since a physiological paracnne system is proposed as a basis for a therapeutic use according to an endocrine mechanism of action. Here, (1–3)IGF-I is used again for the demonstration.

The production of endogenous NMDA receptor antagonists by several peptide systems is novel and the data using (1–3)IGF-I can be used as an application of the developmental aspects and the endocrine mechanism of action.

MATERIALS AND METHODS

The hypothalamic explants of male Wistar rats were studied individually using a static incubation system described earlier (1–3, 9). The total incubation volume of each chamber (0.5 ml) was sampled and renewed every 7.5 min. Using these fractions, the radioimmunoassay of GnRH was performed as described in detail previously (1, 2). The secretion of GnRH was studied either in the absence of any secretagogue or during the 7.5- min exposure to $5.10^{-5}$ M of veratridine, a depolarizing agent opening the Na+channel, or $5.10^{-2}$M of kainate or N-methyl-D, L-aspartate (NMA) which are agonists of distinct subtypes of glutamate receptors. All these products were bought from Sigma, St Louis, Mo. At 25 and 50 days, veratridine was used repeatedly at 37.5-min intervals. At 15 days, veratridine was used at 52.5-min intervals, i.e. beyond the period of refractoriness caused by the inhibitory autofeedback of GnRH(11). The secretory response of GnRH was calculated as the difference between the concentration measured immediately before and during exposure to the secretagogue.

We studied the effects of the in-vitro exposure to increasing concentrations of recombinant hIGF-I (Kabi-Pharmacia, Stockholm, Sweden) or its two subproducts, (1—3)IGF-I (Peninsula, Merseyside, England) and (4–70)IGF-I (Gropep, Adelaide, Australia). We also studied the effects of other peptides. The GnRH fragments and analogs included (1–5) GnRH (UCB, Brussels, Belgium), (2–10)GnRH (Sigma, St Louis, Mo., USA) and (1–9)GnRHa (D-TRP$^6$-PRO$^9$-N-Ethylamide GnRH) a GnRH agonist kindly provided by Dr J Rivier (The Salk Institute, California, USA). The bovine Proinsulin and its subproducts included the C-peptide of insulin and insulin itself (Novo-Nordisk, Copenhagen, Denmark). Finally, the GRF-related peptides included (1–43) rat GRF (Bachern, Bubendorf, Switzerland), (1–37) human GRF (Peninsula, Merseyside, England) and (1–29) human GRF (Kabi Pharmacia, Stockholm, Sweden). AP-5 (DL-2-amino-5-phosphonovaleric acid, Sigma), a selective antagonist at NMDA receptors and DNQX (6,7-dinitroquinoxaline-2,3-dione, Tocris Neuramin, Buckhurst Hill, United Kingdom) a selective antagonist at kainate receptors, were also used. The different peptides or antagonists were used for 15 min, i.e. the 7.5-min fraction before and during exposure to veratridine. We also studied the effects of a single s.c. injection of IGF-I or its subproducts in 15or 50 day-old rats. Then, the animals were sacrificed and the hypothalamic explants studied 25 min after the injection, this interval being required to obtain plasma concentrations of IGF- I sufficient to affect protein metabolism (A. Skottner, personal communication). At that time, the serum was collected for the assay of IGF-I using a method described elsewhere (15) and testosterone was measured as well using a standard RIA (Sorin Biomedica). The concentration of the studied substances resulting in 50% inhibition of the GnRH secretory response (IC$_{50}$) was calculated as described earlier (3, 9) and the data were compared by covariance analysis. The occurrence of significant GnRH secretory pulses was determined using the pulsar program (2, 3).

RESULTS

Legends, results and comments to the figures:

FIG. 1(a–c). In vitro effects of IGF-I-related peptides on GnRH secretion by hypothalamic explants at 15, 25 and 50 days.

GnRH secretory response to depolarizing episodes (veratridine 50 µM for 7.5 min) was studied repeatedly at intervals of 52.5 min at 15 days or 37.5 min at 25 and 50 days. Such study was performed in control conditions or in the presence of increasing concentrations of IGF-I and subproducts, (4–70)IGF-I and (1–3)IGF-I, as well as AP-5, a competitive antagonist at NMDA receptors. Each experiment was preceded and followed by a veratridine challenge in control conditions.

Using hypothalamic explants obtained at 15, 25 or 50 days the secretion of GnRH induced by repeated exposure to veratridine in control conditions does not change throughout the experiment (FIG. 1).

When the explants are incubated in the presence of IGF-I, the secretion of GnRH is not affected at 15 days whereas a dose-related inhibition is observed at 25 and 50 days. The sensitivity to this inhibitory effect is greater at 50 days than at 25 days as indicated by the $IC_{50}$ of IGF-I which are $2.10^{-13}$ and $8-10^{-10}$M, respectively ($p<0.001$). At the 3 ages studied, (4–70)IGF-I does not result in any effect on the GnRH secretion. In contrast, the incubation of the explants with (1–3)IGF-I causes a dose-related inhibition of GnRH secretion. At 25 and 50 days, the $IC_{50}$ of (1–3)IGF-I ($4.10^{-9}$ and $3.10^{-13}$M, respectively) is similar to that obtained using IGF-I. At 15 days, the explants are highly sensitive to the inhibitory effect of (1–3)IGF-I ($IC_{50}$:$1.10^{-13}$M) while they are not affected by IGF-I. At 15, 25 and 50 days, AP-5 results in a dose-related suppression of GnRH secretion ($IC_{50}$:$2.10^{-13}$, $1.10^{-9}$ and $1.10^{-11}$ M, respectively) which parallels the inhibitory effects of (1–3)IGF-I.

As shown in table 1, using 50-day-old explants, (1–3) IGF-I ($10^{-10}$ to $10^{-6}$M) does not change the secretion of GnRH induced by kainate whereas a dose-related inhibition of the GnRH secretion induced by NMA is observed. Noteworthy, on account of the competitive nature of the antagonism at the NMDA receptors, 10–6M of (1–3)IGF-I are required to suppress the NMA-induced secretion of GnRH, whereas $10^{-10}$M of the tripeptide is sufficient to suppress the secretion of GnRH induced by veratridine. This $10^{-10}$M concentration of (1–3)IGF-I can only result in partial inhibition of the GnRH secretory response to veratridine when studied in the presence of NMA at a concentration ($5.10^{-4}$M) which has no effects per se (table 1).

dine for a period of 47.5–107.5 min which is directly related to the dose of IGF-I used. Thereafter, the secretory response of GnRH is progressively recovered. The mean (±SEM) serum concentrations of IGF-I obtained 25 min after the injection of 0, 0.05, 01, 0.2 and 0.5 mg/kg of IGF-I are respectively 799±87, 948±76, 1054±115, 1215±50 and 1740±28 ng/ml. Thus, the IGF-I injection accounts respectively for increases of 19, 32, 52 and 118% in serum IGF-I concentration. The mean serum testosterone concentration is not significantly different in the rats injected with the vehicle (2.5±1.5 ng/mnl) or with 0.1 mg/kg of IGF-I (2.6±1.7 ng/ml). No effect is observed after the injection of 0.1 mg/kg of (4–70)IGF-I whereas 0.004 mg/kg of (1–3)IGF-I results in inhibition of the GnRH response to veratridine (FIG. 2). This inhibition is similar to that seen using 0.1 mg/kg of IGF-I, an equivalent dose on a molar basis. In addition, the spontaneous pulsatile secretion of GnRH from hypothalamic explants of 50-day-old rats is abolished for almost 2 hrs after the s.c. injection of 0.1 mg/kg of IGF-I (data not shown). This period of inhibition is consistent with the effects of the same dose on the secretion induced by veratridine.

FIG. 3(*a–b*). Ex-vivo effects of IGF-I-related peptides on GnRH secretion by rat hypothalamic explants at 15 and 50 days.

The mean±SEM increment of GnRH secretion induced by veratridine ($5.10^{-5}$M for 7.5 min) was studied repeatedly using explants obtained at 15 and 50 days. The experiment protocol is the same as in FIG. 2. The study of the hypothalamic explants of 50-day-old male rats (n =6 in each group) started 25 min after the in-vivo s.c. injection of physiological saline (vehicle) or different dosages of IGF-I, or (1–3)IGF-I. The data obtained at 15 days are opposed to

TABLE 1

In-vitro effects of (1–3)IGF-1 and N-methyl-D,L-asparate (NMA) on GnRH secretion by hypothalamic explants of 50-day-old male rats

| Secretagogue | Controls | +(1–3)IGF-I | | | | +NMA | +NMA $5 \cdot 10^{-4}$ M + (1–3)IGF-I |
|---|---|---|---|---|---|---|---|
| | | $10^{-10}$ M | $10^{-8}$ M | $10^{-7}$ M | $10^{-6}$ M | $5 \cdot 10^{-4}$ M | $10^{-10}$ M |
| Kainate $5 \cdot 10^{-2}$ M | 100 ± 6 | — | 114 ± 14 | 107 ± 10 | 95 ± 12 | — | — |
| NMA $5 \cdot 10^{-2}$ M | 100 ± 7 | 93[b] ± 12 | 73 ± 3 | 43 ± 6 | 14 ± 4 | | |
| Veratridine $5 \cdot 10^{-5}$ M | 100 ± 7 | 11[a] ± 7 | — | — | — | 98 ± 4 | 55[c] ± 3 |

The data % of controls, mean ± SEM (n = 6)
b vs a: p < 0.001, c vs a: p < 0.001

FIG. 2(*a–b*). Ex-vivo effects of IGF-I-related peptides on GnRH secretion by rat hypothalamic explants at 50 days.

The mean±SEM increment of GnRH secretion induced by veratridine ($5.10^{-5}$M for 7.5 min) was studied repeatedly at 30-min intervals. The study of the hypothalamic explants of 50-day-old male rats (n=6 in each group) started 25 min after the in-vivo s.c. injection of physiological saline (vehicle) or different dosages of IGF-I, or 0.1 mg/kg of (4–70)IGF-I or 0.004 mg/kg of (1–3)IGF-I which is equimolar with 0.1 mg/kg of IGF-I.

After a single s.c. injection of 0.5 mg/kg of IGF-I in 50-day-old animals, the in-vitro secretion of GnRH in response to veratridine is markedly inhibited for up to 167.5 min (FIG. 2). IGF-I concentrations of 0.05–0.2 mg/kg result in a suppression of the GnRH secretory response to veratrithat obtained at 50 days to show that IGF-I is only effective at 50 days despite the use of higher doses at 15 days. In contrast, (1–3)IGF-I is effective at both ages. The 50-day data can be seen on FIG. 2 but here they are shown comparatively with those obtained at 15 days.

Figure 4A:
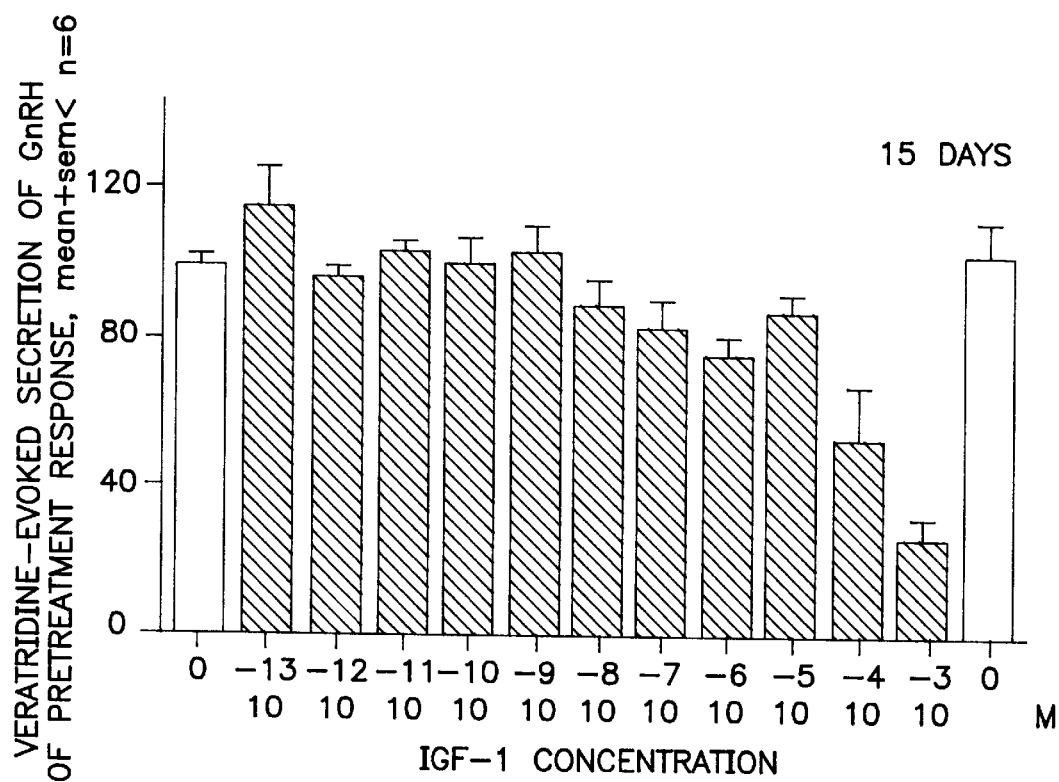
Figure 4B:
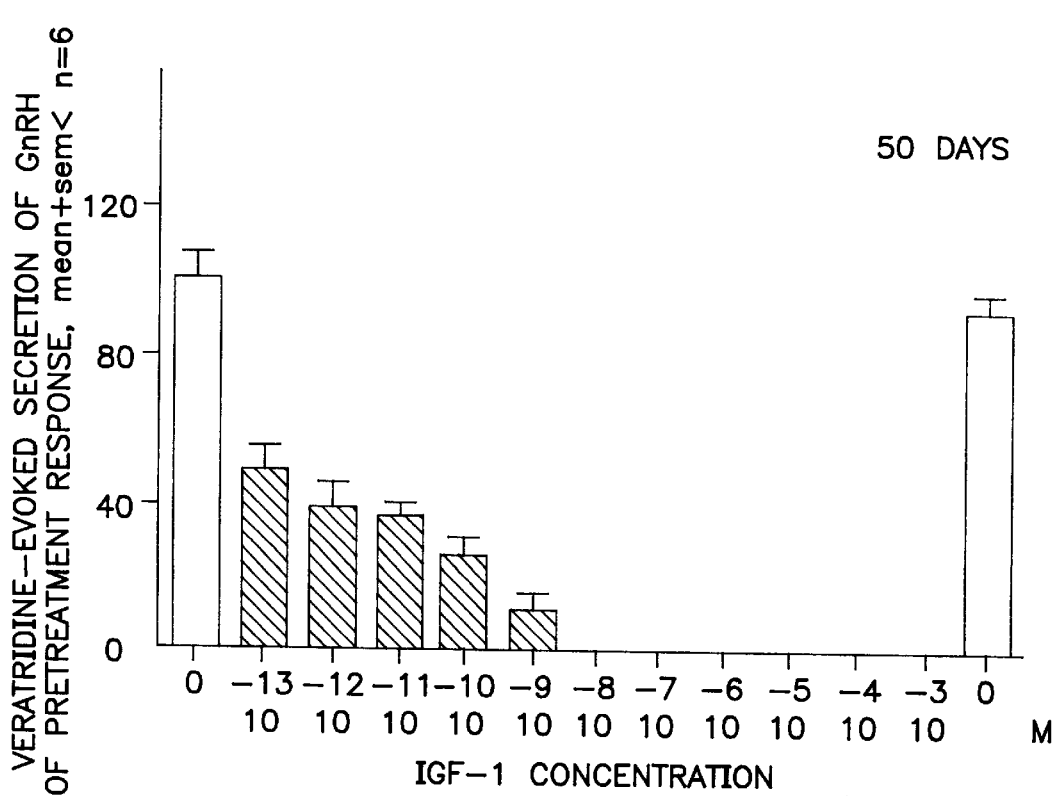

FIG. 4(*a–b*): In-vitro effects of IGF-I on the secretion of GnRH by hypothalamic explants at 15 and 50 days.

The experimental procedure is the same as in FIG. 1. Explants of 15 and 50-day-old rats were used. The Figure shows that using very high concentrations of IGF-I attaining $10^{-4}$ and $10^{-3}$M, it is ultimately possible to get an inhibition of GnRH secretion at 15 days. This suggests that there is a mechanism limiting IGF-I degradation into (1–3)IGF-I at 15 days. The figure illustrates the fact that IGF-I does not result in NMDA receptor antagonism at 15 days, in the immature rat, as long as high concentrations enough are not used. The data confirm the need to use (1–3)IGF-I as NMDA antagonist in the immature animals.

FIG. 5(a–c): In-vitro effects of IGF-I and (1–3)IGF-I on the secretion of GnRH by hypothalamic explants in the presence of peptidase inhibitors.

The experimental procedure is the same as in FIG. 1. Three different inhibitors were used. When used alone, they do not effect GnRH secretory response to veratridine. While (1–3)IGF-I ($10^{-10}$M) results in suppression of GnRH secretion, the effect is prevented by the peptidase inhibitors indicating that IGF-I needs to be degraded to cause the inhibitory effect. The suppressing effect of (1–3)IGF-I on GnRH secretion is not prevented by the peptidase inhibitor. Thus, the inhibitory effect of IGF-I can be prevented by three different peptidase inhibitors, which do not effect the inhibition of GnRH secretion by (1–3)IGF-I. So the necessity of IGF-I to be degraded into (1–3) IGF-I to cause inhibition of GnRH secretion is shown.

FIG. 6(a–b): In-vitro effects of GnRH-related peptides on the secretion of GnRH by hypothalamic explants at 15 and 50 days.

The left panels show representative profiles of GnRH secretion by individual explants of 50-day-old male rats. In control conditions, a depolarization using veratridine is performed every 37.5 min. In the experimental conditions, this is repeated in the presence of different substances including the competitive NMDA receptor antagonist AP-5, the subproducts (1–5) and (2–10)GnRH and the superagonist (1–9)GnRHa. Note that the concentrations used for the (1–9)GnRH agonist are greater.

The right panels represent the GnRH secretory response to veratridine (mean data of 6 individual explants) in relation to the different concentrations of the GnRH-related peptides or the antagonist AP-5. Here, the data are expressed as a percentage of the initial GnRH secretory response obtained in control conditions. As shown in FIG. 6, the veratridine-induced secretion of GnRH is inhibited by (1–5)GnRH in a dose-related manner which is similar to the effect of AP-5. Using other glutamic acid terminating fragment of GnRH such as (1–2)GnRH and (1–6)GnRH, a similar inhibitory effect is obtained (data not shown). Using the superagonist of GnRH, (1–9)GnRHa, GnRH secretion can be inhibited as well, though the $IC_{50}$ ($2\times10^{-10}$M) is significantly higher than that observed using (1–5)GnRH ($5\times10^{-13}$M) . This difference could be related to the relatively reduced rate of degradation of the superagonist versus the native decapeptide GnRH.

FIG. 7(a–c): In-vitro effects of IGF-I, GRF and Insulin-related peptides on the secretion of GnRH by hypothalamic explants.

The experimental procedure is the same as in FIG. 6. Explants of 50-day-old rats were used. Different peptides and their subproducts were used. The (1–37) and (1–29) subproducts of GRF that we used were the human sequence which is not remarkably different from the rat sequence. In contrast, the full (1–43) sequence was the rat GRF because human GRF is very different at the C terminus. Bovine proinsulin, insulin and C-peptide of insulin were also studied.

(1–43)GRF and the glutamic acid-terminating subproduct (1–37)GRF result in a dose-related inhibition of the secretion of GnRH. (FIG. 7). This effect does not seem to be dependent on the GH-releasing activity of those peptides since (1–29)GRF does not affect GnRH secretion while that peptide has retained the GH-releasing activity. Proinsulin and the C-peptide of insulin which has a terminal glutamic acid, are also capable of a dose-related suppression of GnRH secretion. In contrast, the highly bioactive peptide insulin has no effects. As already discussed for IGF-I, it is possible that the inhibitory effects of (1–43)GRF and Proinsulin depend on the endogenous degradation of those peptides into their glutamic acid-terminating subproducts.

FIG. 8(a–b): In-vitro effects of glutamid acid-terminating peptides on the secretion of GnRH induced by NMA and kainate from hypothalamic explants.

The GnRH secretory response induced by the 7.5-min exposure to NMA (upper panel) or kainate (lower panel) was studied using explants of 50-day-old male rats. This study was performed in the presence of glutamic acid-terminating subproducts of different peptides and in the presence of AP-5 and DNQX which are respectively selective antagonists at NMDA and kainate receptors. All these substances wee used at the $10^{-6}$M concentration.

As shown in FIG. 8, the glutamic acid-terminal peptides belonging to the different systems studied result in a marked inhibition of the secretion of GnRH induced by NMA, whereas the kainate-induced secretion of GnRH is not affected. The involvement of the NMDA receptors but not the kainate receptors is further shown by the inhibitory effects obtained using the selective antagonists, AP-5 and DNQX, respectively. (FIG. 8).

FIG. 9: Displacement of tritiated glutamate from hypothalmic membrane by different compounds.

Hypothalmic membrane preparations are used to study the displacement of tritiated glutamate binding in the presence of different compounds. Glutamate is able to displace the binding of the tracer at relatively low $10^{-6}$ to $10^{-8}$ concentrations. IGF-I, (1–3)IGF-I and (1–5)GnRH act as competitors of glutamate binding to hypothalamic membranes. While high concentrations of those compounds are required, it is noteworthy that even higher concentrations of NMA or AP-5 are needed to obtain a displacement of tritiated glutamate bindning. This is because the affinity of tritiated glutamate for the NMDA receptors is less than for the other subtypes of glutamate receptors.

We have also studied the effects of $10^{-12}$ M to $10^{-9}$M of βendorphin and TRH which do exhibit a terminating glutamate. Both these peptides result in 40 to 60% inhibition of the veratridine-induced secretion of GnRH though the effect was not found to be dose-related in this preliminary experiment. Thus the concept developed here could be extended to other glutamic acid terminating peptides.

Preliminary data obtained using patch-clamp studies of hippocampal neurons indicate that different subtypes of glutamate receptors including NMDA and kainate receptors could be antagonized by (1–3)IGF-I.

DISCUSSION

We have thus shown that IGF-I accounts for an inhibitory effect on the secretion of GnRH. This effect is unlikely to be mediated through the classical IGF-I receptors since the secretion of GnRH is not affected by (4–70)IGF-I, a highly bioactive agonist at IGF-I receptors (7). Therefore, it is assumed that, the N-terminal tripeptide, (1–3)IGF-I, could mediate the inhibitory effects of IGF-I on the secretion of GnRH. This hypothesis is supported by the equipotency of the inhibitory effects of IGF-I and (1–3)IGF-I at 25 and 50 days. In addition, the requirement of very high concentrations of IGF-I at 15 days while its (1–3) subproduct is markedly inhibitory at this age and the effect of peptidase inhibitors, show that the inhibitory effects of IGF-I requires its degradation into (1–3)IGF-I, a mechanism which could not operate at 15 days yet. (1–3)IGF-I is more likely to result from enzymatic degradation of IGF-I than from a separate process of biosynthesis. Studies on the human fetal brain cDNA of IGF-I have shown that the aminoterminal truncation should result from a posttranscriptional modification of the peptide (16).

(1–3)IGF-I was suggested earlier to act as a agonist at the NMDA receptors (8). In contrast our data support the activity of (1–3) IGF-I as antagonist at NMDA receptors. In our previous studies using different agonists and antagonists of NMDA and kainate receptors, we have shown that proper activation of the NMDA receptors is a prerequisite to the GnRH secretory pulses occurring either spontaneously or in response to veratridine (2,3,9). Here, we show that the NMA-evoked secretion of GnRH is affected by IGF-I while the kainate-evoked secretion is not. The competitive nature of the antagonism of IGF-I at NMDA receptors is suggested by the relatively low sensitivity to IGF-I at 25 days, a time characterised by a peak activation of the NMDA receptors involved in the secretion of GnRH (3, 9). Also, IGF-I is less active as an inhibitor when the incubation medium is enriched with the agonist NMA. Moreover, IGF-I and its (1–3) subproduct appear to be inhibitors of the GnRH secretion as potent as AP-5, a specific competitive antagonist at NMDA receptors. Finally, glutamate binding to hypothalamic membrane preparation is diplaced by different peptide antagonists.

Our observations are discrepant from those of Hiney et al who reported that IGF-I stimulated the secretion of GnRH from median eminence explants of female rats (17). Such a difference cannot be explained by gender since we found that the GnRH secretion from explants of 30-day-old female rats was inhibited by IGF-I (data not shown). A possible explanation is that Hiney et al used the median eminence terminals of GnRH neurons where the kainate receptors were shown to play a major role (18). In contrast, using a bigger piece of hypothalamus including the arcuate nucleus, we found that the NMDA receptors were critical for the GnRH secretion (1–3, 9). Thus, the physiological significance of these observations could depend on the anatomical site where IGF-I is acting. The paracrine delivery of IGF-I by the brain to these receptors linked to the GnRH neurosecreation is still putative. Alternatively, it is conceivable that the hypothalamus is affected by changes in the plasma concentrations of IGF-I, through an endocrine mechanism. From our data on the acute endocrine effects of IGF-I, we may not infer that the chronic variations in plasma IGF-I concentrations modulate CNS functions. A chronic inhibitory effect of IGF-I on the GnRH secretion is not expected since the male pubertal development occurs between 25 and 50 days of age while circulating IGF-I shows an important increase at the same period (5). However, it is striking that an acute increase of only 19% in serum IGF-I concentrations can results in temporary suppression of the GnRH secretion. Such an effect cannot be explained by a negative feedback effect of increased secretion of gonadal steroids by IGF-I because serum testosterone levels are unchanged. Since the spontaneous pulsatile secretion of GnRH in vitro is acutely suppressed by IGF-I, it is possible that the pulsatile secretion of LH (luteinizing hormone) in vivo would be suppressed as well. This deserves further studies which can be of importance for the therapeutic use of IGF-I.

It is remarkable that IGF-I does not generate any antagonism of NMDA receptors at 15 days of age, a period characterised by a high level of receptors to excitatory amino acids (19, 20). In addition, the occurrence of IGF-I inhibitory effects between 15 and 25 days is coincident with a reduction in number and activity of those receptors (19, 20). It is possible to view the GnRH neurosecretory system and the associated NMDA receptors as a model of the interactions between these receptors and IGF-I in the whole CNS. In this setting, the NMDA receptors are known to play a critical role in neurotoxicity, a process more severe during early postnatal life than in adult animals (21). In agreement with the concept proposed in this paper, it has been reported recently that IGF-I can protect against brain hypoxic-ischemic injury (22) whereas (4–70)IGF-I does not result in such an effect (23). Thus, it can be suggested that IGF-I plays a critical role in CNS as a precursor of (1–3)IGF-I, a possible endogenous antagonist at the NMDA receptors.

The concept of NMDA receptor antagonism by glutamic acid-terminating peptides can be extended to peptide systems different from IGF-I, since the subproducts of GnRH, GRF and proinsulin account for similar effects. This suggests that any peptide with a terminal glutamic acid resulting from direct biosynthesis or from degradation of precursor peptides, could act as an antagonist of glutamate receptors (NMDA subtype). In physiological conditions, these peptides are probably involved in a paracrine or autocrine effect at their site of biosynthesis. They can act as inhibitory autoregulators of their secretion when this process depends on activation of NMDA receptors. Such a mechanism can be involved in the autofeedback of GnRH that we described earlier (11). A similar mechanism can play a role in the control of GRF secretion. As already discussed, the possible physiological relevance of IGF-I related peptides is different on account of the widespread distribution of this peptide and its relatively high concentrations in peripheral blood. Therefore (1–3)IGF-I can be regarded as an ubiquitous endogenous antagonist at glutamate receptors, which originates from paracrine or endocrine production. Finally, it is possible that the glutamate receptors which have a well established role in the CNS, play some role in other body organs such as the pancreas where C-peptide of insulin can provide an endogenous antagonist of those receptors.

CONCLUSION

Here, the effects of IGF-I and its subproducts, (1–3)IGF-I and (4–70)IGF-I have been studied, either given in vivo as a single S.C. injection or used in vitro, on the secretion of GnRH by hypothalamic explants. At the 3 ages studied (15, 25 and 50 days), (4–70)IGF-I does not show any effect. At 50 days, the in vivo administration or the in vitro use of IGF-I results in a dose-related inhibition of the GnRH secretion induced by veratridine, a depolarizing agent. In addition, the spontaneous pulsatile secretion of GnRH in vitro is transiently suppressed after the in vivo administration of IGF-I. (1–3)IGF-I results in an inhibitory effect similar to that of IGF-I. At 25 days, IGF-I and (1–3)IGF-I show the same effects as at 50 days though higher concentrations are required. At 15 days, IGF-I does not show any effect whereas a potent inhibition of GnRH secretion is observed using (1–3) IGF-I either in vivo or in vitro. The glutamate-terminal subproducts of other peptide systems such as (1–5)GnRH, (1–37)GRF and C-peptide of insulin result in inhibitory effects similar to that of (1–3)IGF-I. These effects parallel that of AP-5, a competitive antagonist at NMDA receptors. In addition, the studied peptides suppress the GnRH secretion induced by NMA but not that induced by kainate and they cause displacement of tritiated glutamate from hypothalamic membrane preparations. These data indicate that glutamate-terminal subproducts of different peptide systems play a role as antagonist at NMDA receptors. This can result from a local, paracrine effect. An endocrine effect is also possible since the acute systemic administration of IGF-I results in a suppression of GnRH secretion, presumably through a competitive antagonism at NMDA receptors by (1–3)IGF-I resulting from IGF-I degradation. This process seems to develop between 15 and 25 days of age, indicating the importance of developmental aspects.

REFERENCES

1 Bourguignon J P, Gérard A, Franchimont P: Direct activation of GnRH secretion through different receptors to neuroexcitatory amino acids. Neuroendocrinology 1989;49:402–408.

2 Bourguignon J P, Gérard A, Mathieu J, Simons J, Franchimont P: Pulsatile release of gonadotropin releasing hormone from hypothalamic explants is restrained by blockade of N-methyl-D, L aspartate receptors. Endocrinology 1989;125:1090–1096.

3 Bourguignon J P, Gérard A, Alvarez Gonzalez M L, Franchimont P: Neuroendocrine mechanism of onset of puberty: sequential reduction in activity of inhibitory and faccilitatory N-Methyl-D-Aspartate receptors. J Clin Invest 1992;90:1736–1744.

4 Baskin D G, Wilcox B J, Figlewicz D P, Dorsa D M: Insulin and insulin-like growth factors in the CNS. TINS 1988;11:107–111.

5 Handelsman D J, Spaliviero J A, Scott C D, Baxter R C: Hormonal regulation of the peripubertal surge of insullin-like growth factor-I in the rat. Endocrinology 1987;120:491–496.

6 Sara V R, Carlsson-Skwirut C, Andersson C, Hall E, Sjögren B, Holmgren A, Jörnval H H: Characterization of somatomedins from human fetal brain: identification of a variant form of insulin-like growth factor I. Proc. Natl Acad Sci USA 1986;83:4904–4907.

7 Szabo L, Mottershead D G, Ballard F J, Wallace J C: The bovine insulin-like growth factor (IGF) binding protein purified from conditioned medium requires the N-terminal tripeptide in IGF-1 for binding. Biochem Biophys Res Commun 1988;151:207–214.

8 Sara V R, Carlsson-Skwirut C, Bergman T, Jörnvall H, Roberts P J, Crawford M, Håkansson L N, Civalero I, Nordberg A: Identification of gly-pro-glu (GPE), the aminoterminal tripeptide of insulin-like growth factor I which is truncated in brain, as a novel neuroactive peptide. Biochem Biophys Res Commun 1989;165:766–771.

9 Bourguignon J P, Gérard A, Alvarez Gonzalez M L, Fawe L, Franchimont P: Gonadal independent developmental changes in activation of N-methyl-D-aspartate receptors involved in gonadotropin-releasing hormone secretion. Neuroendocrinology 1992;55:634–641.

10 Carone F A, Stetler-Stevenson M A, May V, LaBarbera A, Flouret G: Differences between in vitro and in vivo degradation of LHRH by rat brain and other organs. Am J Physiol 1987;253:E317-E321.

11 Bourguignon J P, Gérard A, Franchimont P: Maturation of the hypothalamic control of pulsatile gonadotropin-releasing hormone at onset of puberty. II. Reduced potency of an inhibitory autofeedback. Endocrinology 1990;127:2884–2890.

12 Mason G A, Bissette G, Nemeroff C B: Effects of exctitotoxic amino acids on pituitary hormone secretion in the rat. Brain Res 1983;289:366–369.

13 Sasaki A, Sato S, Yumita S, Hanew K, Miura Y, Yoshinaga K: Multiple forms of immunoreactive Growth Hormone-Releasing Hormone in human plasma, hypothalamus and tumor tissues. J Clin Endocrinol Metab 1989;68:180–185.

14 Baekkeshov S, Aanstoot H J, Christgau S, Reetz A, Solimena M, Cascalho M, Folli F, Richter-Olesen H, DeCamilli P, Camilli P D: Identification of the 64K autoantigen in insulin-dependent diabetes as the GABA-synthesizing enzyme glutamic acid decarboxylase. Nature 1990;347:151–156.

15 Bourguignon J P, Gérard A, Deby-Dupont G, Franchimont P: Effects of growth hormone therapy on the developmental changes of follicle stimulating hormone and insulin-like growth factor-I serum concentrations in Turner syndrome. Clin Endocrinol 1993, 39:85–89.

16 Sandberg A C, Engberg C, Lake M, Van Holst H, Sara V R: The expression of insulin-like growth factor I and insulin-like growth factor II genes in the human fetal and adult brain and in glioma. Neurosci Lett 1988;93:114–119.

17 Hiney J K, Ojeda S R, Lees Dees W: Insulin-like growth factor I: a possible metabolic signal involved in the regulation of female puberty. Neuroendocrinology 1991;54:420–423.

18 Donoso A O, Lopez F J, Negro Vilar A: Glutamate receptors of the non N-methyl-D-aspartic acid type mediate the increase in luteinizing hormone-releasing hormone release by excitatory amino acids in vitro. Endocrinology 1990;126:414–420.

19 Nicoletti F, Iadarola M J, Wuroblewski J T, Costa E: Excitatory amino acid recognition sites coupled with inositol phospholipid metabolism: developmental changes and interaction with alpha-1-adrenoreceptors. Proc And Acad Sci USA 1986;83:1931–1935.

20 Hestrin S: Developmental regulation of NMDA receptor-mediated synaptic currents at a central synapse. Nature (Lond.) 1992;357:686–689.

21 McDonald J W, Silverstein F S, Johnston M V: Neurotoxicity of N-methyl-D-aspartate is markedly enhanced in developing rat central nervous system. Brain Res 1988;459:200–203.

22 Gluckman P, Klempt N, Guan J, Mallard C, Sirimanne E, Dragernow M, Klempt M, Singh K, Williams C, Nikolics K: A role for IGF-I in the rescue of CNS neurons following hypoxic-ischemic injury. Biochem Biophys Res Commun 1992;182:593–599.

23 Gluckman P D, Guan J, Williams C, Bielharz E, Sirimanne E, Klempt N: The role of insulin-like growth factor-I (IGF-1) incentral neuronal rescue in "The role of insulin-like growth factors in the nervous system". Arlington, Va., November 1992, p18 (abstr.).

I claim:

1. Method for inhibiting the effect of glutamate on glutamate-receptor-controlled cells by administration of an effective of glutamic acid-terminating peptide antagonists at glutamate receptors.

2. Method for inhibition on NMDA-receptorcontrolled cells by administration of peptide antagonists at NMDA receptors.

3. Method according to claim 2 for preventing NMDA-receptor mediated excitatory effects.

4. Method according to claim 1 for inhibition of the function of neurons or glial cell in the central nervous system.

5. Method according to claim 1 in which the antagonists at NMDA receptors comprises glutamic acidterminating peptides.

6. Method according to claim 1 in which the antagonist is chosen among (1–5)GnRH, (1–3)IGF-I, (1–37)GRF and C-peptide of insulin.

7. Method according to claim 1 for inhibiting the GnRH secretion.

8. Method according to claim 1 in which a medicament is administered which comprises (1–3) IGF-I.

9. Method according to claim 1 in which a medicament is administered systemically.

10. Method according to claim 1 in which a medicament is administered locally.

11. The method of claim 3 wherein said excitatory effects are selected from the group consisting of release of neurotransmitter, release of peptide, and toxic effects resulting in cell injury or death.

* * * * *

UNITED STATES PATENT AND TRADEMARK OFFICE
CERTIFICATE OF CORRECTION

PATENT NO. : 5,804,550
DATED : September 8, 1998
INVENTOR(S): Bourguignon

It is certified that error appears in the above-identified patent and that said Letters Patent is hereby corrected as shown below:

Title page, item [22] should read:

PCT Filed: May 16, 1994---.

Title page, item [86] should read:

PCT No.: PCT/SE94/00454

§ 371 Date: Nov. 9, 1995

§ 102(e) Date: Nov. 9, 1995

Title page, item [87] should read:

PCT Pub. No.: WO94/26301

PCT Pub. Date: Nov. 24, 1994

Signed and Sealed this

Fifth Day of January, 1999

Attest:

Attesting Officer

*Acting Commissioner of Patents and Trademarks*